United States Patent [19]

Hakkinen

[11] Patent Number: 4,986,269
[45] Date of Patent: Jan. 22, 1991

[54] RESPIRATION THERAPY APPARATUS

[75] Inventor: Taisto Hakkinen, Hameenlinna, Finland

[73] Assignee: Etela-Hameen Keuhkovammayhdistys R.Y., Finland

[21] Appl. No.: 432,540

[22] Filed: Nov. 7, 1989

Related U.S. Application Data

[63] Continuation-in-part of Ser. No. 25,146, filed as PCT FI86/0005 on May 20, 1986, published as WO86/06969 on Dec. 4, 1986, abandoned.

[30] Foreign Application Priority Data

May 23, 1985 [FI] Finland .................................. 852073

[51] Int. Cl.⁵ ............................................. A61M 16/18
[52] U.S. Cl. ............................ 128/204.23; 128/200.21; 128/204.21; 128/204.25; 128/204.26
[58] Field of Search ........................ 128/200.21, 203.12, 128/204.21, 204.23, 204.25, 204.26, 205.24, 204.19

[56] References Cited

U.S. PATENT DOCUMENTS

| | | | |
|---|---|---|---|
| 3,537,448 | 11/1970 | Liston | 128/200.21 |
| 3,653,379 | 4/1972 | Glenn | 128/204.28 |
| 3,662,751 | 5/1972 | Barkalow et al. | 128/204.25 |
| 3,664,337 | 5/1972 | Lindsey et al. | 128/200.21 |
| 3,739,776 | 6/1973 | Bird et al. | 128/204.25 |
| 4,471,773 | 9/1984 | Bunnell et al. | 128/200.21 |
| 4,570,631 | 2/1986 | Durkan | 128/204.23 |

Primary Examiner—David A. Wiecking
Assistant Examiner—Eric P. Raciti
Attorney, Agent, or Firm—Steinberg & Raskin

[57] ABSTRACT

The invention concerns a respiration therapy apparatus used as a drug atomizer and/or a so-called respirator and/or as an oxygen dispenser. In the apparatus of the invention, administration to a patient of oxygen or air is discontinued, at the latest, when the exhalation phase begins. This has been implemented in the apparatus of the present invention by utilizing a pressure pick-up (22) observing differential pressure of the flow and which further provides control of an electromagnetic valve (23) which is disposed to close and to open a pressure line (16). At commencement of the inspiration phase, the differential pressure is transmitted over a signal connection (99) to the pressure pick-up (22). The pressure pick-up (22) further controls the electromagnetic valve (23), opening the pressure line (16). The pressure pick-up (22) measuring differential pressure has been connected, in accordance with the present invention, over a signal connection (19, 39, 59 or 99) to an oxygen mask, to oxygen whiskers (30), to an atomizer (50), or to a respirator (80).

8 Claims, 8 Drawing Sheets

RESPIRATION THERAPY APPARATUS

CROSS REFERENCE TO RELATED APPLICATION

The present application is a continuation-in-part of co-pending U.S. application Ser. No. 025,146, now abandoned filed as PCT FI86/00053 on May 20, 1986, published as WO86/06969 on Dec. 4, 1986, now abandoned.

BACKGROUND OF THE INVENTION

The present invention concerns a respiration therapy apparatus intended for persons suffering from respiratory diseases, for indisposed persons, or for unconscious persons, and employed as a respirator and/or as a drug atomizing apparatus and/or as an oxygen dispensing apparatus conforming to the patient's respiration. The respiration therapy apparatus comprises an oxygen or air supply tube connected to regulating means. An air or oxygen line coming from an oxygen mask or from oxygen whiskers, and an air or oxygen line coming from a drug atomizer are further connected to this regulation means. Alternatively, air or oxygen lines which come from respirator means comprising a mouthpiece, an exhalation valve, a drug atomizer and an injector, are connected to said regulating means, a second one of said air or oxygen lines being directly connected to the injector and a first one of said air or oxygen lines being connected to the drug atomizer, advantageously over a regulating valve, for adding drug spray to the oxygen or air flow.

Various kinds of respiration therapy apparatuses intended for persons suffering from respiratory diseases, for indisposed persons, or for unconscious persons, are known in the prior art, the respiration therapy apparatus then comprising a drug atomizer, a supply pressure source communicating with the drug atomizer for conducting air or oxygen, an injector communicating with the drug atomizer, and separate regulating valves for controlling the atomizing rate of the drug atomizer or the respiration pressure. In drug atomizers of the prior art, the flow rate of the flowing air or oxygen is controllable.

Regulating valves are known in the art through which the air or oxygen can be conducted. It is possible with the aid of electrically controlled magnetic valves, or of magnetic valve controlling means, to effect control of the operating period of the respiration therapy apparatus in conformity with the patient's breathing rhythm. Similarly, it is possible with the aid of separate timer means to effect regulation of the resting period of the respiration therapy apparatus to conform to the patient's breathing rhythm.

Respiration therapy apparatus of the prior art can then be controlled with the aid of press buttons or the equivalent in a manner such that the operation of the respirator is paced to be appropriate for the patient, for instance specifically by pressing a button.

By the same token, respirators are known in the art, e.g. through an earlier Finnish patent application No. 83-0059 of the assignee, where the respirator is used as atomizing means. The period of operation and period of rest of the drug atomizer can be controlled with timer means, or by pacing with finger pressure on a press button, to conform to a breathing rhythm appropriate for the particular patient, and by regulating the atomizing rate of the drug atomizer with the aid of a pressure regulator, provided with a pressure gauge, inserted in the supply pressure line.

It is also previously known that an inhalation dispenser is provided with atomizing commencement time control for the purpose of selecting the time of commencement of atomizing to be advantageous for each individual patient, at the beginning of the inspiration period. This apparatus arrangement is known through the earlier Finnish patent application No. 84-3769 to the same assignee. Through the same Finnish patent application of the assignee, an inhalation dispenser is also known incorporating an inspiration flow rate control for setting a desired magnitude, the inspiration flow rate advantageous for each individual patient.

The apparatus just described cannot be used in conjunction with oxygen whiskers or masks as oxygen supplying means, and cannot serve, in this simple design, as an atomizer and respirator apparatus.

The drawback of oxygen supplying means of the prior art, can again be seen in the circumstance that the oxygen also flows during the exhalation period, causing unnecessary irritation of the patient's nostrils. It is thus understood that the patient is disturbed by the continuous oxygen flow, and it is understood that the detrimental consequence of this continuous oxygen or air flow is highly wasted consumption. Drug substance is also wasted, and the patient's environment becomes polluted.

SUMMARY OF THE INVENTION

The respirator design of the present invention eliminates all drawbacks which have been previously described. These drawbacks have been avoided by implementing a respirator of the present invention with a pressure pick-up, so that there is a signal connection to the pressure pick-up. The signal connection has further been taken out through a connector from the regulating means. This pick-up indicating the pressure of the respiration flow, is further applied to control a control valve which governs the oxygen or air flow going to the patient. The pick-up observes the pressure change arriving through the signal connection and it observes the moment when the patient commences his inspiration. The pick-up then acts on the control valve and opens the oxygen or air flow passage.

By the same token, the pick-up observes, through the signal connection, the commencement of the patient's exhalation phase, at which time the pressure pick-up further acts on the control valve, whereby the valve closes the oxygen or air passages. With this apparatus arrangement, supply of oxygen or air or drugs to the patient during the patient's exhalation phase, is avoided.

The apparatus design of the present invention, which may expressly be used both as atomizer means, as oxygen administration means, and as a respirator, may operate at different pressure levels. It is this versatility which enables the signal connection of the invention to be taken out from the control units and carried to different targets. The use of the apparatus design of the present invention as multi-purpose means, in operation at low and high pressure levels, is thereby rendered feasible.

The present invention is principally characterized by the respiration therapy apparatus comprising a pressure pick-up and a separate connection extending to the pressure pick-up arranged to close and open the air or oxygen supply pressure line which, over a valve, communicates with the oxygen or air line, so that when the patient's inspiration takes place, the pressure pick-up observes the pressure change in the inspiration air caused by the commencement of this inspiration phase, the pick-up having been arranged thereupon to open the valve, and similarly at commencement of the patient's exhalation, the pressure pick-up has been arranged to control the valve so that the air or oxygen pressure line is closed.

Basically, the present invention is directed to a respiration therapy apparatus intended for persons suffering from respiratory diseases, for indisposed persons, or for unconscious persons, and which is used as a respirator (IPPB) and/or as drug atomizing means and/or as oxygen dispensing means conforming to the patient's respiration. The respiration therapy apparatus comprises an air or oxygen supply tube connected to a control unit, with this control unit being further connected to an air or oxygen line coming from an oxygen mask or from oxygen whiskers.

Alternatively, the control unit is connected to an oxygen or air line coming from a drug atomizer or to associated oxygen or air lines coming from a respirator having a mouthpiece, an exhalation valve, a drug atomizer and an injector. A first one of these oxygen or air lines is connected to the drug atomizer, preferably over a regulating valve, for adding atomized drug spray to the oxygen or air flow, while the second line is connected directly to an injector.

The respiration therapy apparatus comprises a pressure pick-up and a separate connection leading to the pressure pick-up which is arranged to close and open the air or oxygen supply pressure line which communicates over a valve with the oxygen or air lines, so that when a patient's inspiration is taking place, the pressure pick-up senses or observes the change of pressure in the inspiration air caused by the commencement of this inspiration phase, at which the pressure pick-up has been arranged to open the valve, while respectively at commencement of the patient's exhalation, the pressure pick-up has been arranged to control the valve so that the air or oxygen pressure line is closed.

The control unit comprises timing means which regulate the oxygen or air flow coming to the atomizer, to the oxygen whiskers, or to the oxygen mask. The signal or control variable coming from the pressure pick-up has been arranged, counted from commencement of the inspiration phase, to start the count of the timing means provided in the control unit. In this timing means, the maximum time during which the valve is opened and admits the air or oxygen flow to the oxygen whiskers, to the oxygen masks, to the atomizer means or to the respirator, has been pre-set.

Accordingly, to summarize, the present invention is directed to respiration therapy apparatus intended for individuals suffering from respiratory diseases, for indisposed individuals, or for unconscious individuals, the respiration therapy apparatus being used as a respirator (IPPB) or as means for atomizing a drug, and the respiratory apparatus comprising a control unit,
an oxygen or air supply pressure tube connected to the control unit,
a respirator,
a first and a second oxygen or air line by means of which the control unit is connected to the respirator,
the respirator comprising a mouthpiece, an exhalation valve, a drug atomizer and an injector,
a pressure pick-up,
a separater connector leading from the pressure pick-up to the flow of oxygen or air from the control unit to the respirator,
valve means disposed in the flow of oxygen or air, the pressure pick-up arranged to control opening and closing of the valve means,
whereby the flow of oxygen or air from the control unit to the respirator is controlled with the aid of the pressure pick-up, so that when inspiration of an individual is taking place, the pressure pick-up senses change of pressure in inspirational oxygen or air caused by commencement of an inspirational phase, and the pressure pick-up is arranged to open the valve means by which connection of the supply pressure line to the control unit is opened, and
at commencement of exhalation, the valve means are adjusted by way of the pressure pick-up to a position such that the connection to the supply pressure line is closed.

The respiration therapy apparatus additionally comprises timing means provided in the control unit and arranged so that a signal or a control variable coming from the pressure pick-up is arranged, counting from commencement of the inspirational phase, to start the count of the timing means, with maximum time during which the valve means of the control unit connected to the timing means is opened and admitting the air or oxygen flow from the control unit to the respirator being pre-set in the timing means.

The control unit valve means additionally comprise both a first valve and a second valve, both of which are arranged to be controlled by the pressure pick-up, and said second valve being arranged to be controlled via electronics of the timing means, whereby connection from the pressure line to the first line passing from the control unit to the respirator is opened and closed by way of the first valve, and connection from the pressure line to the second line passing from the control unit to the respirator is opened and closed by way of the second valve, so that one of the valves opens and closes the line through which drug atomizing from the drug atomizer of the respirator is effected while the atomized drug is mixed with the air or oxygen conducted along the other line, and at commencement of the inspiration, the other line is opened or controlled by the pressure pick-up, and, at the same time, said one line is opened or controlled by the pressure pick-up via the timing means electronics, the maximum time the drug is atomized being pre-set in the timing means.

BRIEF DESCRIPTION OF THE DRAWINGS

The present invention will be described in greater detail below, with reference to the accompanying drawings, in which.

DESCRIPTION OF THE PREFERRED EMBODIMENTS

Figures 1, 2:
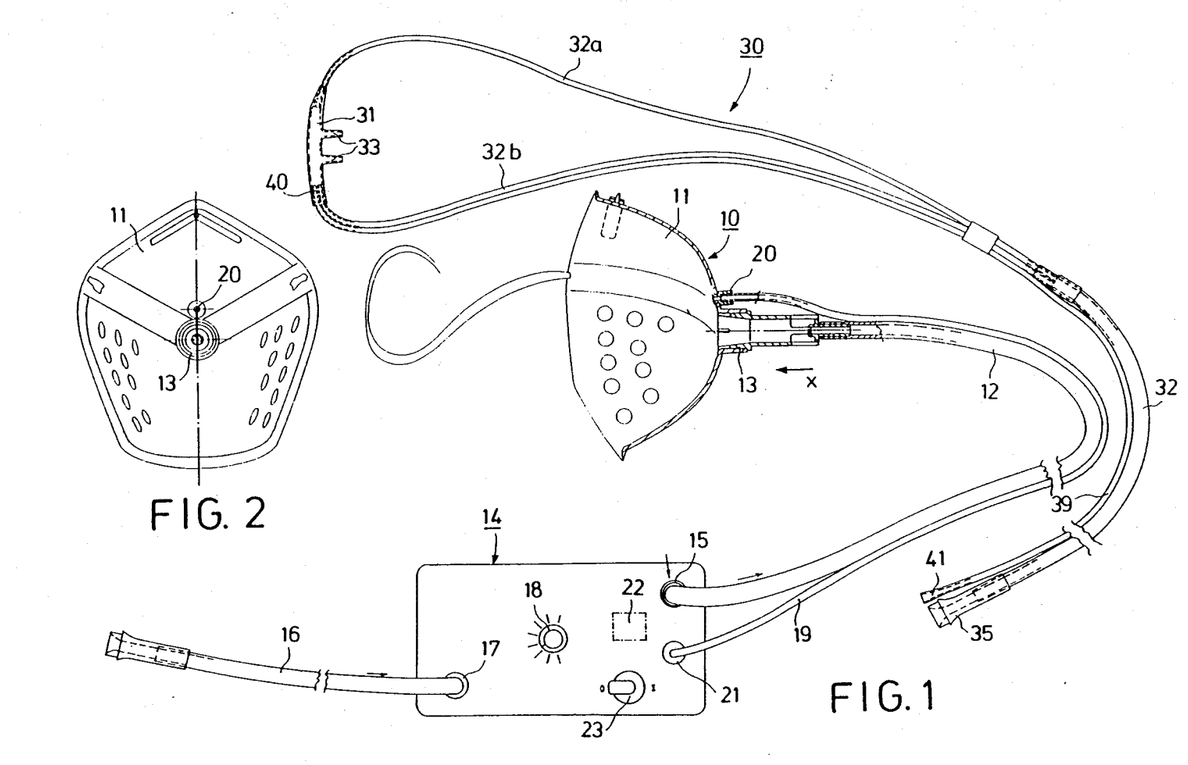
FIG. 1 is a schematic view of a respirator according to the invention, of the oxygen or air tube, and of the signal connection extending to the pressure pick-up, this connection being attached to a face mask. Moreover, separate oxygen whiskers have been depicted in this figure.
FIG. 2 illustrates a face mask, as viewed from the front and in a direction X indicated in FIG. 1.

In FIG. 1, a respiration therapy apparatus is depicted. In the figure, reference numeral 10 indicates a face mask, with numeral 11 indicating a part of the mask to be placed against a face of an individual, this mask part being connected through an air or oxygen tube 12 to a control unit 14. The air or oxygen tube 12 is connected over a connector 13 on the mask 11 to the mask part proper 11. A connector 15 similarly connects the tube 12 with the control unit proper 14.

The supply pressure tube, supplying oxygen or air, is indicated by reference numeral 16. This tube 16 has been connected to the control unit 14 with the connector 17. The control unit 14 comprises the oxygen or air flow operating time control 18. The apparatus of the invention comprises a signal connection 19 leading to a pressure pick-up, this connection being carried from the control unit 14 along with the tube 12 to the mask part proper 11 through the connector 20.

The connector 21 connects the signal connection 19 leading to the pressure pick-up with the control unit proper 14. Reference numeral 22 schematically represents the pressure pick-up or differential pressure transducer, located in the control unit 14. The current supply to the apparatus can be interrupted by operating the switch 23.

The current to the respiration therapy apparatus and also suitably to its control unit 14, may be conveyed either from a storage battery, from a dry cell battery, or from the electric mains.

Reference numeral 30 denotes oxygen whiskers. These whiskers may conduct air or oxygen into a patient. The oxygen line or air line 32 branches into two lines 32a and 32b. These branches 32a and 32b are further connected to a nostril connector 31 comprising parts 33 entering the nostrils. The connection of the air or oxygen line 32 to the control unit 14 is indicated with reference numeral 35. Reference numeral 39 indicates the signal connector leading to the pressure pick-up.

The connection of the branches 32a and 32b of the air or oxygen line with the nostril connector 31, is represented by reference numeral 40. Connector 41 is the connection with the control unit 1 of the signal connection 39 leading to the pressure pick-up.

Figure 3:
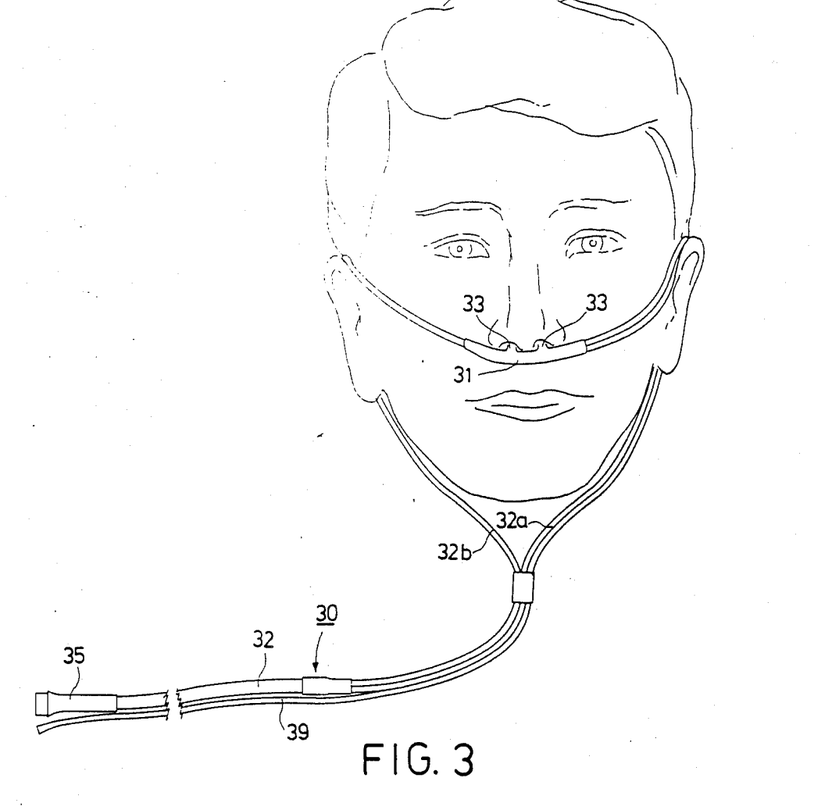
FIG. 3 illustrates oxygen whiskers attached to a patient, the connection to be carried to the pressure pick-up being incorporated in this figure.

FIG. 3 illustrates the oxygen whiskers 30 attached to a patient.

Figure 4:
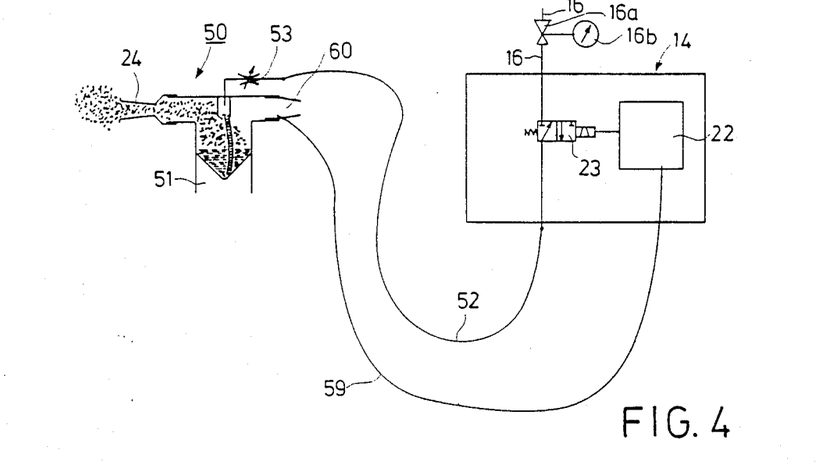
FIG. 4 illustrates a respirator according to the invention, provided with pressure pick-up and signal connection and used as atomizing means.

FIG. 4 schematically illustrates the use of the respiration therapy apparatus 10 as atomizing means for drug dispensing. Reference numeral 50 indicates drug atomizing means. A supply pressure tube 52 leading to the drug atomizer is connected to the drug atomizer 51. Control of atomizing rate takes place through the valve 53. Reference numeral 59 represents the connection extending to the pressure pick-up 22. The pick-up 22, in its turn, controls an electromagnetic valve 23, namely the opening and closing thereof. Through this valve 23, the oxygen or air is carried along the supply pressure tube 52.

The conical connector 60 of the signal connection is attached to the drug atomizer 51. The air or oxygen supply pressure line 16 extends to the valve 23. A supply pressure valve 16a, and, in association therewith, a supply pressure gauge 16b, are incorporated in this line 16. The drug atomizer 51 is provided with a mouthpiece 24, through which the flow enters the patient.

The signal connection 59 leading to the pressure pick-up has been connected to the conical connector 60 on the drug atomizer 51. The operation of the unit is such that when the patient inhales through the mouthpiece 24, there is a flow through the conical connector 60 whereby the pressure falls in this connector 60. This pressure drop is observed by the pressure pick-up 22, and the pressure drop is transmitted through the signal connection 59 to the pick-up 22. The signal connection is appropriately a length of plastic tubing.

The pick-up 22 transmits the information, controlling the electromagnetic valve 23 and opening a connection from the supply pressure line 16 to the supply pressure tube 52 extending to the drug atomizer 51. In other words, a connector 59 is connected with the pressure pick-up 22, and is further connected to a conical connector 60 on the atomizer 51. Thereby, an atomized drug spray will, in the course of the patient's inspiration, be admixed with the air entering through the conical connector 60, the atomized spray being produced by the air or oxygen flow to the drug atomizer 51 taking place along the supply pressure tube 52.

The control unit 14 may furthermore comprise means by which the maximum time of drug atomizing is regulated. If the inspiration phase exceeds this maximum time, the maximum time controller shuts off the communication from the pressure line 16 to the supply pressure tube 52 and the atomizing process is interrupted. In any other case, when the patient commences exhalation through the mouthpiece 24, the pressure in connector 59 increases, and this pressure rise is observed by the pressure pick-up 22, which then controls the electromagnetic valve 23 and shuts off the connection between the supply passage 16 and the supply pressure tube 52, the atomizing process ceasing forthwith.

In other words, as illustrated in FIG. 4, the respiratory apparatus comprises a control unit 14, an oxygen or air supply pressure tube 16 connected to the control unit 14, a respirator 50, an oxygen or air line 52 by means of which the control unit 14 is connected to the respirator 50, and the respirator 50 comprises a mouthpiece 24, a drug atomizer 51, and a connector 60.

The respiration therapy apparatus additionally comprises a pressure pick-up 22, a separate connector leading from the pressure pick-up 22 to the flow of oxygen or air from the control unit 14 to the respirator 50, and valve means 23 disposed in the flow of oxygen or air, the pressure pick-up 22 being arranged to control opening and closing of the valve means 23, whereby the flow of oxygen or air from the control unit 14 to the respirator 50 is controlled with the aid of the pressure pick-up 22, so that when inspiration of an individual is taking place, the pressure pick-up 22 senses change of pressure in inspirational oxygen or air caused by commencement of an inspirational phase, and the pressure pick-up 22 is arranged to open the valve 23 by which connection of the supply pressure line 16 to the controlled unit 14 is opened, and at commencement of exhalation, the valve means 23 are adjusted by way of the pressure pick-up 22 to a position such that the connection to the supply pressure line 16 is closed.

The respiration therapy apparatus additionally comprises timing means 94, 97 provided in the control unit 14 and arranged so that a signal or a control variable coming from the pressure pick-up 22 is arranged, counting from commencement of the inspirational phase, to start the count of the timing means 94, 97, with maximum time during which the valve means 23 of the control unit 14 connected to the timing means 94, 97 is opened and admitting the air or oxygen flow from the control unit 14 to the respirator 50 being pre-set in the timing means 94, 97. The controlled unit valve 23, which is arranged to be controlled by the pressure pick-up 22, is also arranged to be controlled via electronics of the timing means 94, 97, whereby connection from the pressure line 16 to the line 52 passing from the control unit 14 to the respirator 50 is opened and closed by way of the valve 23, so that the valve 23 opens and closes the line 52 through which drug atomizing from the drug atomizer 51 of the respirator is effected, while the atomized drug is mixed with the air conducted from the atmosphere via the connector 60, and, at commencement of the inspiration, the line 52 is opened or controlled by the pressure pick-up 22, via timing means 94, 97 electronics, the maximum time the drug is atomized being pre-set in the timing means 94, 97.

Figure 5:
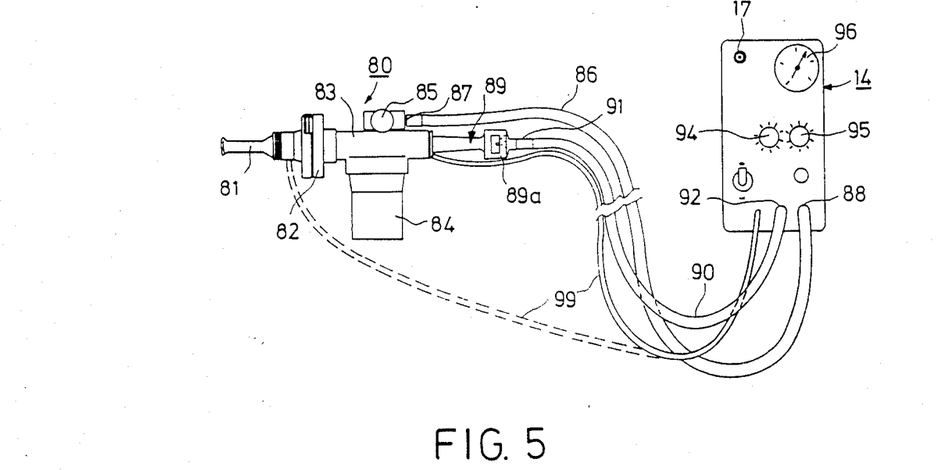
FIG. 5 illustrates an elevational view of a respiration therapy apparatus according to the invention which is used as a respirator (IPPB)

FIG. 5 illustrates, in elevational view, use of a respiration therapy apparatus as a true respirator. A connector 99 is associated with the pressure pick-up 22 and is, at one end thereof, connected to the end adjacent to the atomizing means 83 and injector 89 in the respirator 80, or is connected to the mouthpiece 81 itself. The respirator, now indicated with reference numeral 80, comprises a mouthpiece 81, an exhalation valve 82, and an atomizer 83. From the control unit 14, a supply pressure line 86 for oxygen or air runs over the connector 87 to the atomizer 83. The supply pressure line 86 is connected over the connector 88 with the control unit 14. The flow connector 90 is connected over the connector 92 with the control unit 14, and over the connector 91 with the injector 89, i.e. with its injector nozzle 89a. The injector 89 is further joined with the body of the atomizer 83.

Figure 6:
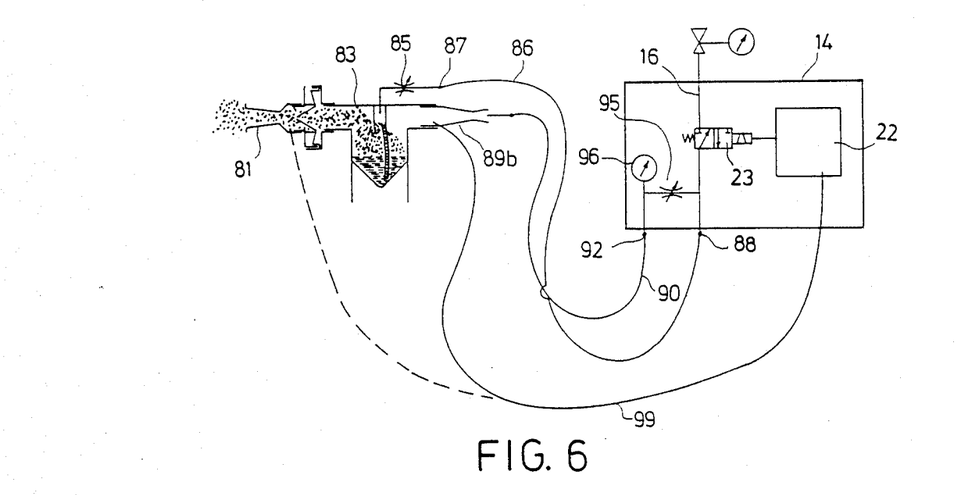
FIG. 6 is a schematic view of the apparatus of FIG. 5, with the alternative placements of the other end of the signal connection being illustrated in this figure.

The control arrangement of the invention is furthermore composed of a pressure pick-up 22, appropriately located in the control unit 14. From the pressure pick-up 22 and from the control valve 14, the signal connection 99 lead either to the mouthpiece 81 or to the atomizing means 83, and in this case suitably to its conical connector. The control unit 14 moreover comprises timer means 94 for the time of operation of the atomizer and a respiration pressure regulator, suitably a regulating valve 95. The control unit 14 further comprises a gauge 96 indicating the respiration pressure. The gauge 96 indicating the respiration pressure is connected, as shown in FIG. 6, to the flow connector 90.

The respiration pressure regulating valve 95 may be connected either directly to the flow connector 90 or to the line leading to this connector 90. When the patient's inspiration is taking place, the pressure pick-up 22 through the signal connection 99 observes the change of pressure and controls the electromagnetic valve 23, as in the embodiment of FIG. 4. When the patient's exhalation commences, the pressure rises at the signal connector 99. The pressure pick-up 22 observes this change and controls the electromagnetic valve 23, shutting off the pressure line. The signal connection 99 may be connected either to the conical connector 89b of the atomizer 83, or directly to the mouthpiece 81 extending to the patient.

The connection 99, 59 coming from the pressure pick-up 22 is connected, at its opposite ends, with a part 89, 60 having a conical cross-section.

The pressure pick-up 22 may also be disposed so that it is located directly in the oxygen or air flow entering the patient. In that case, an electrical signal is conducted from the pressure pick-up 22 along the signal connection to the control unit 14 and further to the electromagnetic valve 23. Most appropriately however, the signal connection is a flexible tube and the pressure pick-up has been disposed to be located expressly in the control unit 14. The changes of pressure are then transmitted along the hollow tube to the pressure pick-up 22. The oxygen or air lines, or connectors, are suitably pieces of plastic tubing consisting of some plastic material.

A signal connection has been carried out from the control unit 14 and has, at one end thereof, been connected to the pressure pick-up 22 and, at the other end thereof, connected to a therapy apparatus consistent with each therapeutic measure.

Figure 7:
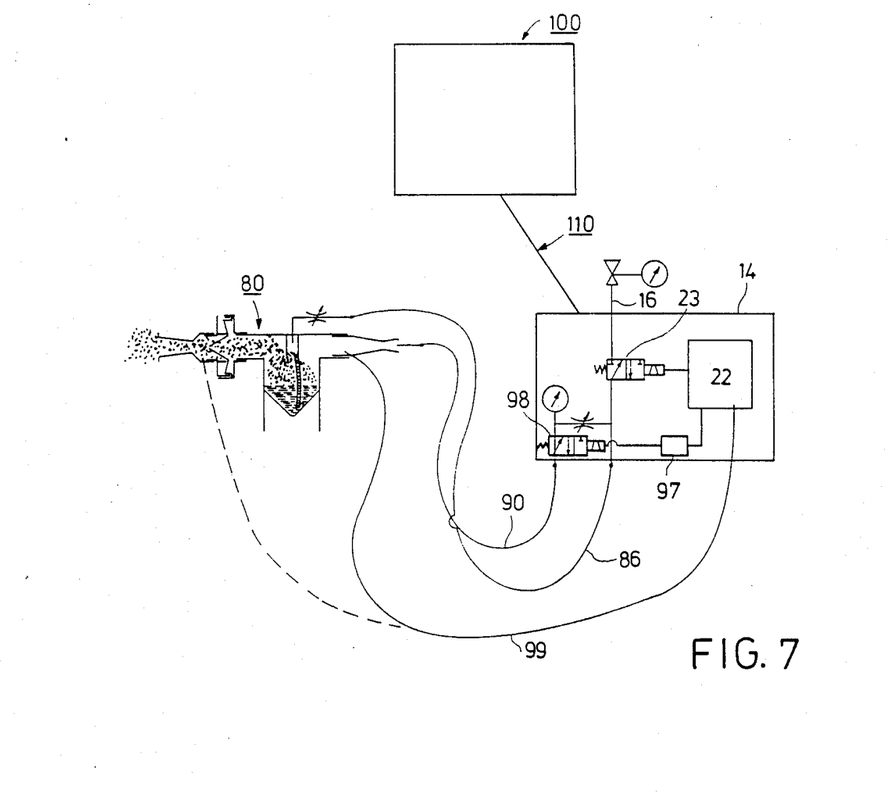
FIG. 7 schematically illustrates the connecting of a computer to the respiration therapy apparatus, and in which furthermore, a design is presented in which two valves have been employed.

A design is presented in FIG. 7 in which, in addition to the valve 23, another valve 98 is also employed, this valve too, appropriately being an electromagnetic valve. The valve 98 has been placed in the flow connector 86, or in the control unit 14 in a manner such that it communicates with the line 86. The pressure pick-up 22 controls the valve 98, either directly or over electronic circuitry 97. The latter may suitably consist of timer means. In that case, it becomes possible to time the opening of the line 90 and the opening of the line 86 to the pressure line 16 to be as desired, and favorable from the therapeutic point of view.

In FIG. 7, the connecting of a computer, suitably a micro-processor, to the respiration therapy apparatus of the invention, has also been illustrated. The computer or equivalent has been indicated with reference numeral 100. The computer is, by one or several cables, connected to the respiration therapy apparatus of the invention. This signal line between the computer and the respiration therapy apparatus has been denoted, in general, with reference numeral 110.

The computer has been arranged, with the aid of a program stored therein, to place the respiration therapy apparatus of the invention into operation and out of operation. The computer 100 may simultaneously control one or several respiration therapy apparatuses. In the latter case, one person is able to program the therapy schedules individually for each patient. The computer may equally be programmed to operate the respiration therapy apparatus of the invention, in a manner such that with the aid of a program stored in the computer's memory, the therapeutic variables of the respiration therapy apparatus, such as respiration pressure, drug atomizing, etc., are controlled. A data line or data lines, carried in a suitable manner from the computer, and which have been denoted in general with reference numeral 110, are connected to the control unit 14. A computer 100 has been depicted in FIG. 7 as connected over a data line or data lines 110, to a respiration therapy apparatus according to the invention.

The data line or data lines 110 has/have been connected directly to the control unit 14.

The computer 100 may be arranged to control the valve 98, which is suitably an electromagnetic valve. The computer 100 may be arranged to control the valves 23 and 98 either separately, or to control both valves 23 and 98 in dependence on other another, as specified in each case in the program that has been stored. The computer 100 may be made to control the valve 98 over the supply electronics 97, suitably timer means. The computer 100 has been disposed to control the valve 98 and/or the valve 23, so that the connection from the supply pressure line 16 to the flow connector 90 and/or to the flow connector 86 is opened.

In the present invention, the control unit 14 comprises, in addition to a first valve 23, a second valve 98 which is advantageously an electromagnetic valve and which communicates with the supply pressure line 86. The pressure pick-up 22 is arranged either directly or over electronic circuitry, most preferably timing means 97, to control the valve 98, whereby the opening of the supply pressure line going to the patient from the control unit 14 to communicate with the pressure line 16, can be timed as desired and appropriate from a therapeutic point of view.

Figure 7A:
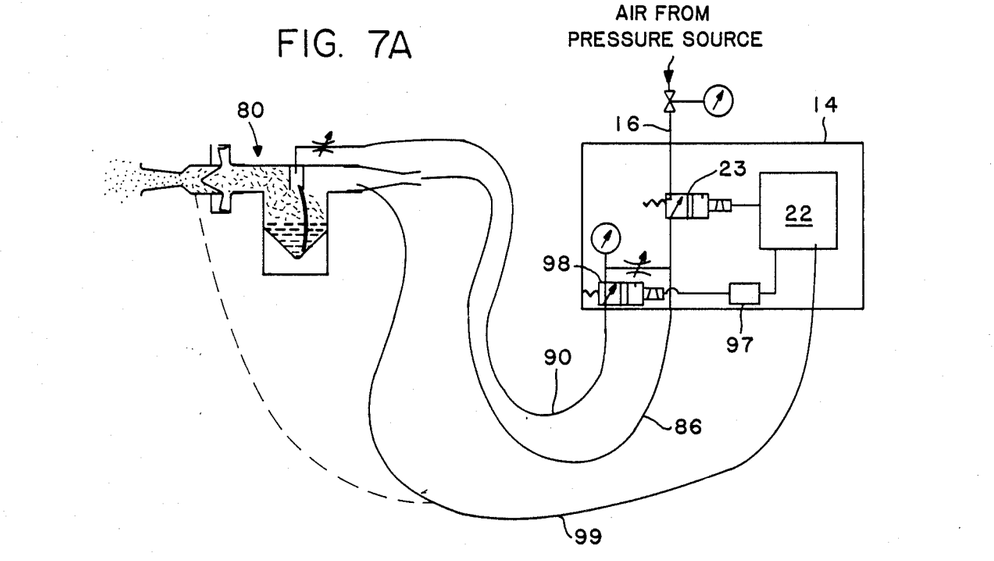
FIG. 7A is a schematic illustration of one embodiment of respiration therapy apparatus in accordance with the present invention.
Figure 7B:
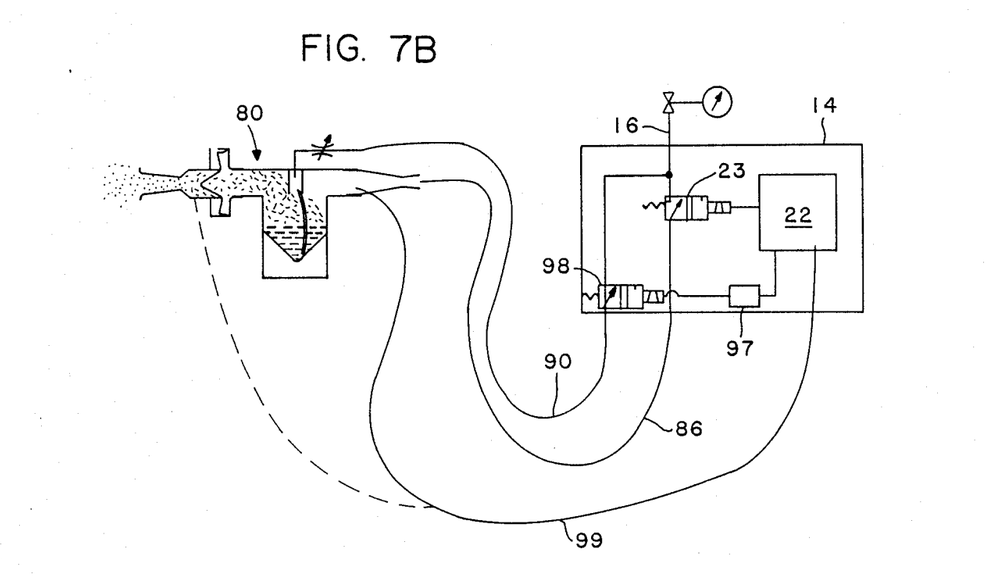
FIG. 7B is a schematic illustration of another embodiment of respiration therapy apparatus in accordance with the present invention.

FIGS. 7A and 7B illustrate two alternative embodiments of the respiration therapy apparatus in accordance with the present invention. In the embodiment illustrated in FIG. 7A, the valves 23 and 98 are connected in series, with the air output of the first valve 23 being passed as air input to the second valve 98, and the air input of the first valve 23 being connected to the pressure air source. In the second embodiment illustrated in FIG. 7B, the valves 23 and 98 are connected in parallel. Similar components as in the other previously-illustrated embodiments of the present invention, have been denoted by the same reference numerals in FIGS. 7A and 7B.

Figure 8:
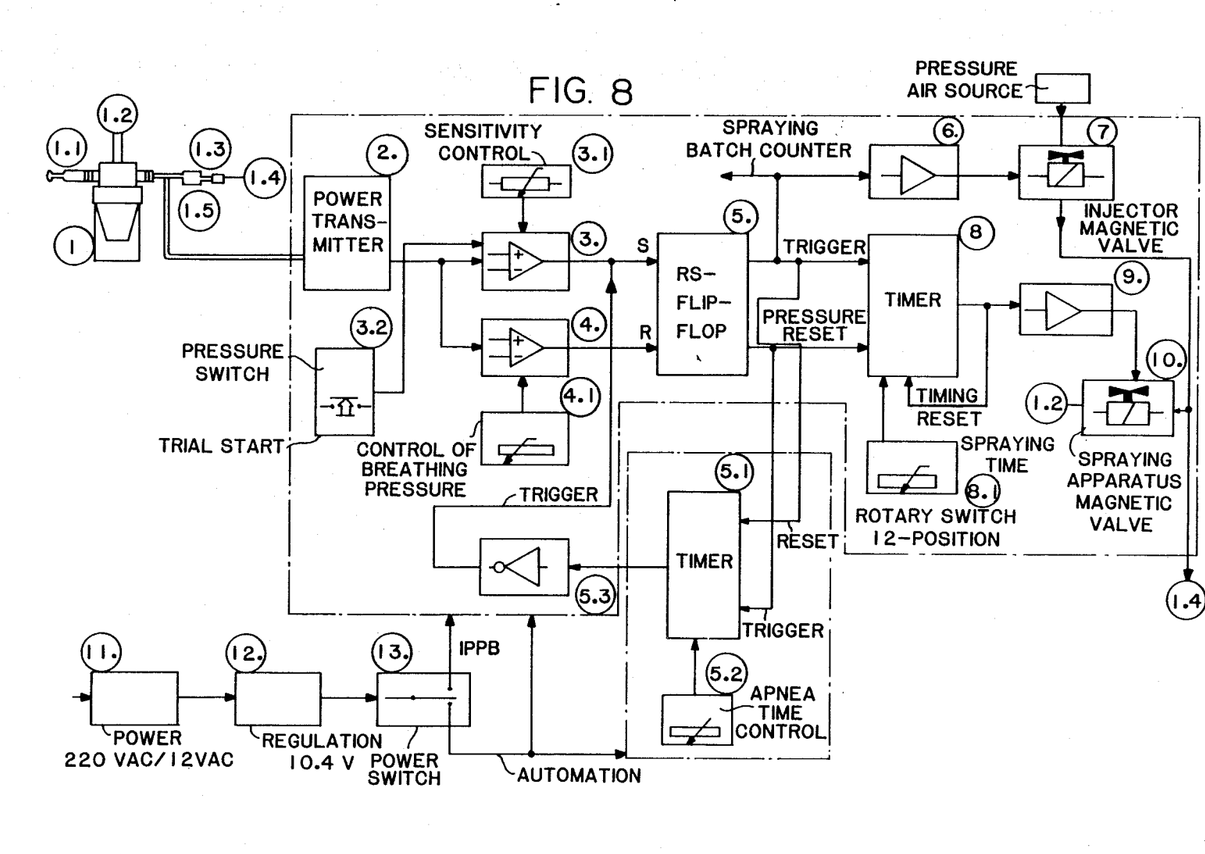
FIG. 8 is a schematic illustration of an electronic system including timing means for operating the embodiment of FIG. 7A.
Figure 9:
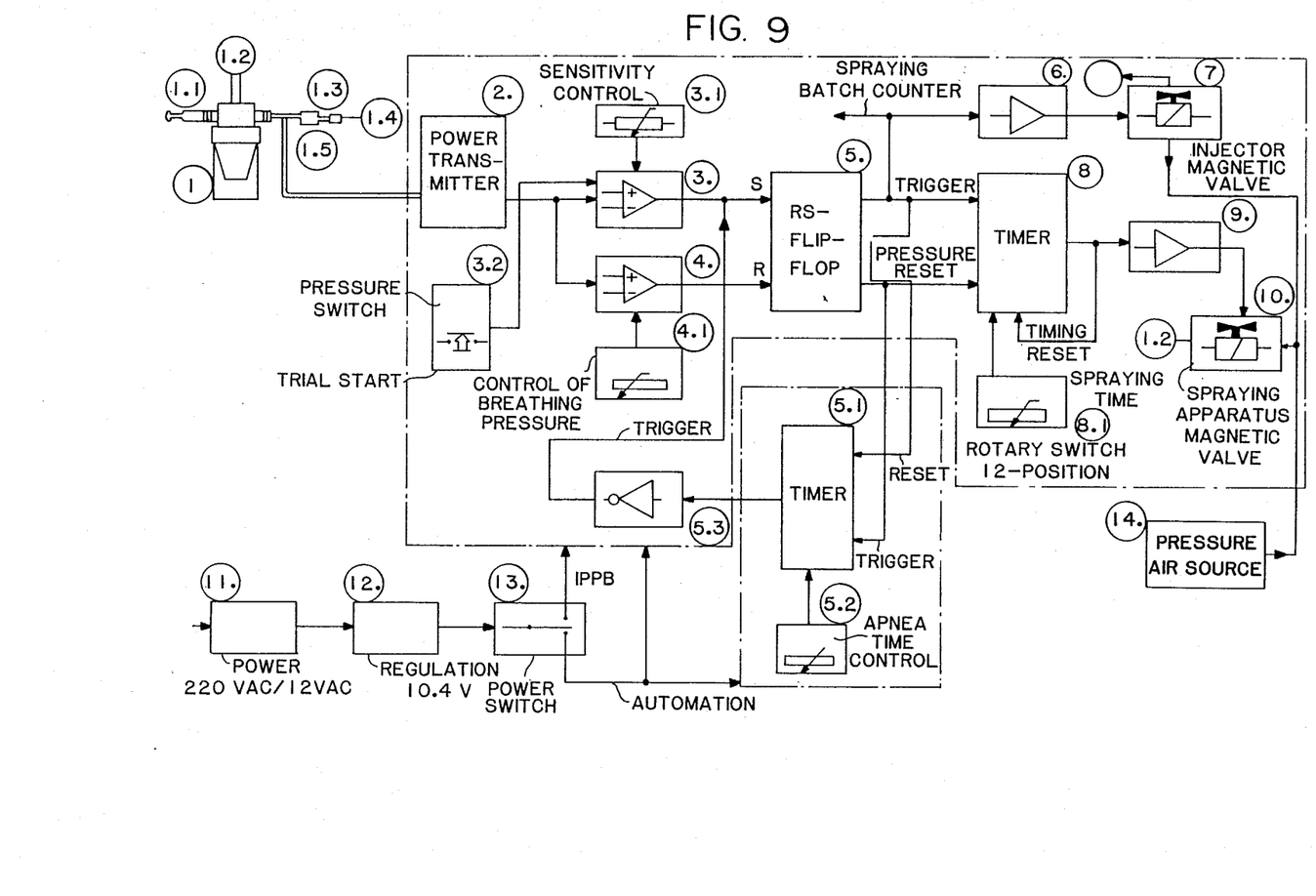
FIG. 9 is a schematic illustration of an electronic system including timing means for operating the embodiment of FIG. 7B.

FIG. 8 illustrates the electronic schema or system for operating the embodiment of FIG. 7A, while FIG. 9 illustrates the electronic schema or system for operating the embodiment of FIG. 7B. The electronic schema or systems of FIGS. 8 and 9 are principally the same, and can also be easily adapted to any of the other specific embodiments of the present invention herein.

More specifically, with reference to both FIGS. 8 and 9, the apparatus of the present invention comprises the following components as denoted in these two figures, as follows:

SPRAYING APPARATUS

When a user breaths by means of a mouthpiece 1.1, a vacuum is produced during inhalation, and overpressure is produced while breathing out or exhaling into the spraying apparatus 1. Pressurized air 14 required for the spraying, enters an upper part 1.2 of the spraying apparatus, controlled by a magnetic valve 10. The pressurized air 14 required for overpressure treatment enters, guided by a magnetic valve 7, an injector 1.3 through a connector 1.4. The quantity of the flow of the pressurized air can be controlled with the injector 1.3.

PRESSURE TRANSMITTER

Through a connector 1.5 of a pressure hose of a sensor in the injector 1.3, variations of the breathing pressure are conducted into a pressure transmitter or pressure pick-up 2. A voltage message is obtained from the pressure transmitter 2, the size of the message being dependent upon the value of breathing pressure. The voltage message to be obtained in the inhalation phase is guided to a triggering circuit 3, the triggering sensitivity of which can be controlled by means of a potentiometer 3.1. The trigger pulse sets the trigger output of an RS-flip-flop 5 to the upper position. This signal is reinforced in a circuit 6 controlling the pressurized air entering the injector 1.3 by means of a magnet valve 7. The same pulse triggers a timer 8 which guides the magnet valve 10 of the spraying pressure.

The pressurized air required in overpressure treatment, enters the spraying apparatus through the injector 1.3 until the pressure within the spraying apparatus reaches the same level as has been set by a potentiometer 4.1.

RESET

In this instance, the circuit 4 resets the RS-flip-flop 5 and the circuit 6 guides the injector magnet valve 7 to become closed, whereby pressurized air will no longer flow into the injector 1.3.

The timer 8 controlling the spraying pressure becomes reset at the same instant, and the spraying pressure ceases to flow when the magnet valve 10 is controlled to close. From the triggering output of the RS-flip-flop 5, there is a connection to the inhalation/spraying batch counter as illustrated in FIGS. 8 and 9.

TIMER

The spraying apparatus/magnet valve 10 is in operation, at the most, for the period which has been set by a rotary switch 8.1 (0.2 sec. to 3 sec.). Thereby, the timer-circuit 8 resets itself while being time-controlled. The timing circuit may, however, be reset in pressure-controlled state prior to the resetting time, if the pressure level required for the overpressure treatment is achieved before the termination of the spraying time. The output circuit of the timing circuit is reinforced in a circuit 9 which controls the spraying apparatus-magnet valve 10.

APNEA-PERIOD

The means are provided with a three-position power switch 13 which, in an automatic position, switches the apnea-timer 5.1 into operation. The timer 5.1 controls the time which is taken since a set inhalation pressure level is achieved, to the beginning of the next inhalation step. The controlling time (APNEA period) can be controlled by meter 5.2, varying from 2 sec. to 20 sec. If the apparatus user is not breathing with a determined apnea period, then the timer 5.1 emits, with the aid of a power amplifier 5.3, a trigger pulse to the RS-flip-flop 5, whereby the injector and the spraying apparatus/magnet valves automatically operate.

The magnet valves are not operated by the automatic operation, if the length of the breathing period of the user is less than the determined apnea time.

TRIAL START

With a button switch 3.2 situated in said means, the operation of said means can be tested before its actual use. The mouthpiece 1.1 of the spraying apparatus can thereby be replaced by an air bag, in order to achieve the level of the predetermined breathing pressure.

POWER SUPPLY

For the power supply, a power supply unit 11 (220 VAC/12 VDC) is reserved, to provide pulsating direct current which is regulated 12 by the electronics card of said means. The regulating voltage is 10.4 V.

POWER SWITCH

When the three-positioned power switch 13 is in its center position, the means are not operative. When the switch is in the IPPB position, the means operates as a normal overpressure treatment and inhalation treatment means.

When the switch is in automatic position, the means act together with the apnea time monitoring. In the IPPB position, the green signal light LED is ON. In the automatic position, the red signal light LED is ON.

Figure 10:
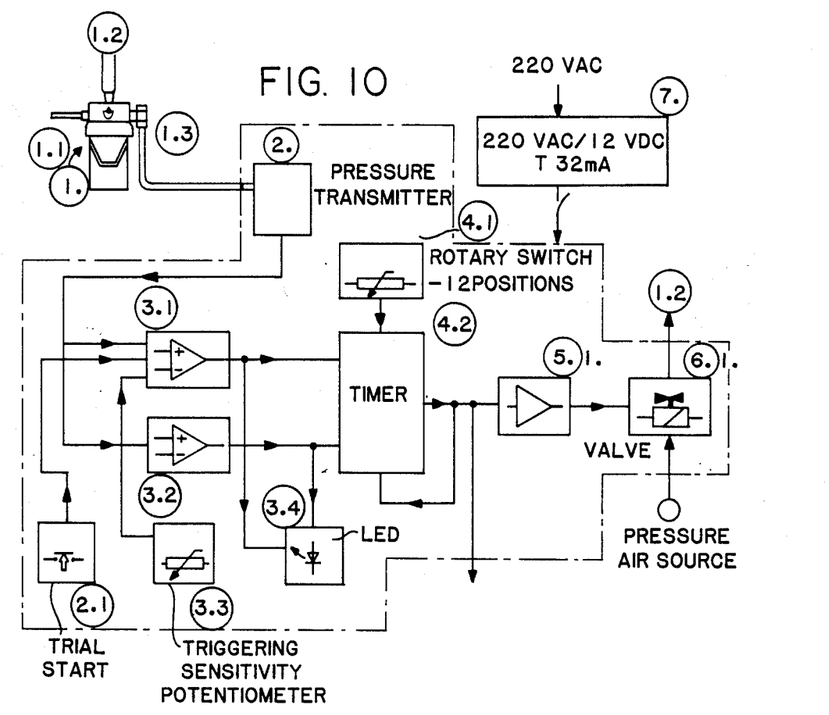
FIG. 10 is a schematic illustration of an electronic system for operating the embodiment of FIG. 4.

The following description is with respect to the embodiment of FIG. 4 with reference to the electronic diagram shown in FIG. 10.

SPRAYING APPARATUS

When a user breaths by means of a mouthpiece 1.1, vacuum is produced by the inhalation, and over pressure while breathing out into the spraying apparatus 1.

The pressurized air required for the spraying enters the upper part 1.2 of the spraying apparatus 1 controlled by a magnet valve 6.1.

PRESSURE PICK-UP OR PRESSURE TRANSMITTER

The variations of the breathing pressure are conducted into a pressure pick-up or pressure transmitter 2 through a connector 1.3. A voltage signal is obtained from the pressure transmitter 2, the size of which is dependent on the value of the breathing pressure. The voltage signal which is obtained in the inhalation phase is guided by a triggering circuit 3.1; 3.2, the triggering sensitivity of which can be controlled by means of a potentiometer 3.3.

After the triggering, the magnet valve 6.1 opens, controlled by a timer 4.2. The triggering takes place when the patient inhales. A yellow LED signal light goes on when the inhalation phase exceeds the triggering level. When the timer circuit has been triggered, it is on that time which is adjusted (0.26 . . . 3 s) via a switch 4.1. There are twelve different time positions in the switch. A timer output signal is reinforced in a circuit 5.1, which provides a control current to the valve 6.1. The timer resets itself after a sufficient time period.

The timer circuit may, however, be reset in pressure controlled state prior to the resetting time, if the inhalation phase is over before the termination of the spraying timer period, which is adjusted via the timer.

A resetting pulse of exhalation comes from the circuit 3.2. When the timer is reset by pressure, the LED light goes off. There is a connection line from the output of the timer 4.2 to a spraying batch counter.

The operation can be tested by a button switch 2.1 before its actual use.

The power supply unit is marked 7.1.

The preceding description of the present invention is merely exemplary, and is not intended to limit the scope thereof in any way.

What is claimed is:

1. Respiration therapy apparatus intended for individuals suffering from respiratory diseases, for indisposed individuals, or for unconscious individuals, said respiration therapy apparatus being used as a respirator (IPPB) or as means for atomizing a drug or for dispensing air or oxygen, and said respiratory apparatus comprising a control unit (14), an oxygen or air supply pressure line (16) connected to said control unit (14), a respirator (80), a first and a second oxygen or air line by means of which said control unit is connected to said respirator (80), said respirator comprising a mouthpiece, an exhalation valve, a drug atomizer and an injector, a pressure pick-up (22), a separate connector leading from said pressure pick-up (22) to a flow of oxygen or air from said control unit (14) to said respirator (80), valve means disposed in the flow of oxygen or air, said pressure pick-up (22) arranged to control opening and closing of said valve means, whereby the flow of oxygen or air from said control unit (14) to said respirator (80) is controlled with the aid of said pressure pick-up (22), so that when inspiration of an individual is taking place, said pressure pick-up (22) senses change of pressure in inspirational oxygen or air caused by commencement of an inspirational phase, and said pressure pick-up is arranged to open said valve means by which a connection of said supply pressure line (16) to said control unit (14) is opened, and at commencement of an exhalation phase, said valve means are adjusted by way of said pressure pick-up (22) to a position such that the connection to said supply pressure line (16) is closed, said respiration therapy apparatus additionally comprising timing means (94, 97) provided in said control unit (14) and arranged so that a signal or a control variable coming from said pressure pick-up (22) is arranged, counting from commencement of the inspirational phase, to start a count of said timing means (94, 97), with maximum time during which said valve means of said control unit (14) connected to said timing means (94, 97) is opened and admitting the air or oxygen flow from the control unit (14) to the respirator (80) being pre-set in said timing means (94, 97), wherein said valve means comprises both a first valve (23) and a second valve (98), both of which are arranged to be controlled by said pressure pick-up (22), and said second valve (98) is arranged to be controlled via electronics of said timing means (94, 97), whereby connection from said pressure line (16) to said first line passing from the control unit (14) to said respirator (80) is opened and closed by way of said first valve (23), and connection from said pressure line (16) to said second line passing from said control unit (14) to said respirator (80) is opened and closed by way of said second valve (98), so that one of the first valve or the second valve opens and closes said oxygen or air pressure line through which drug atomizing from said drug atomizer of said respirator is effected while an atomized drug is mixed with air or oxygen conducted along one of the first or the second oxygen or air lines, and at commencement of the inspiration, said one of the first or the second oxygen or air lines is opened or controlled by said pressure pick-up (22) and, simultaneously time, said oxygen or air supply pressure line is opened or controlled by said pressure pick-up (22) via said timing means (94, 97) with a maximum time the drug is atomized being pre-set in said timing means (94, 97).

2. The apparatus according to claim 1, additionally comprising a signal connection with a first and second end connected, at the first end thereof, to said pressure pick-up (22) and at the second end thereof to said respirator, said signal connection being carried out from said control unit (14).

3. The apparatus according to claim 2, wherein said pressure pick-up (22) is disposed or located in said control unit (14).

4. The apparatus according to claim 1, wherein said first valve (23) is an electromagnetic valve.

5. The apparatus of claim 3, additionally comprising a connector connecting said pressure pick-up (22) with said respirator (80).

6. The apparatus according to claim 5, wherein said connector (99, 59), coming from said pressure pick-up (22) is connected at another end thereof with a part (89, 60) of said respirator (80) having a conical cross-section.

7. The apparatus according to claim 4, wherein said pressure pick-up (22) is disposed to be locally directed along the oxygen or air flow entering the individual, and additionally comprising a signal connection along which said pressure pick-up (22) conducts an electrical signal to said control unit (14) and further to said electromagnetic valve (23).

8. Respiration therapy apparatus intended for individuals suffering from respiratory diseases, said respiratory apparatus comprising a control unit (14), an oxygen or air supply pressure line (16) connected to said control unit (14), a respirator (50), an oxygen or air line (52) by means of which said control unit (14) is connected to said respirator (50), said respirator (50) comprising a mouthpiece (24), a drug atomizer (51), said respiration therapy apparatus additionally comprising a pressure pick-up (22), a separate connector leading from said pressure pick-up (22) to a flow of oxygen or air from said control unit (14) to said respirator (50), valve means (23) disposed in the flow of oxygen or air, said pressure pick-up (22) arranged to control opening and closing of said valve means (23), whereby the flow of oxygen or air from said control unit (14) to said respirator (80) is controlled with the aid of said pressure pick-up (22), so that when inspiration of an individual is taking place, said pressure pick-up (22) senses change of pressure in inspirational oxygen or air caused by commencement of an inspirational phase, and said pressure pick-up (22) is arranged to open said valve means (23) by which a connection of said supply pressure line (16) to said control unit (14) is opened, and at commencement of an exhalation phase, said valve means (23) are adjusted by way of said pressure pick-up (22) to a position such that the connection to said supply pressure line (16) is closed, said respiration therapy apparatus additionally comprising timing means (94, 97) provided in said control unit (14) and arranged so that a signal or a control variable coming from said pressure pick-up (22) is arranged, counting from commencement of the inspirational phase, to start a count of said timing means (94, 97), with maximum time during which said valve means of said control unit (14) connected to said timing means (94, 97) is opened and admitting the air or oxygen flow from the control unit (14) to the respirator (50) being pre-set in said timing means (94, 97), wherein said valve means (23), which is arranged to be controlled by said pressure pick-up (22), is also arranged to be controlled via said timing means (94, 97), whereby connection from said pressure line (16) to said line (52) passing from the control unit (14) to said respirator (50) is opened and closed by way of said valve (23), so that the valve (23) opens and closes said oxygen or air pressure line (52) through which an atomized drug from said drug atomizer of said respirator is effected while the atomized drug is mixed with air conducted from atmosphere via a connector (60), and at commencement of the inspiration, said oxygen or air supply pressure line (52) is opened or controlled by said pressure pick-up (22), via said timing means (94, 97) with a maximum time the drug is atomized being pre-set in said timing means (94, 97).

* * * * *